United States Patent [19]

Hoffmann et al.

[11] Patent Number: 4,769,028
[45] Date of Patent: Sep. 6, 1988

[54] PHARMACEUTICAL PRODUCT, IN MEDICAL BANDAGE FORM

[75] Inventors: Hans R. Hoffmann; Reinhold Meconi, both of Neuwied; Michael Wolff; Horst Zerbe, both of Monheim, all of Fed. Rep. of Germany

[73] Assignees: Lohmann GmbH & Co. KG, Neuwied; Sanol Schwarz GmbH, Monheim, both of Fed. Rep. of Germany

[21] Appl. No.: 886,401

[22] Filed: Jul. 17, 1986

Related U.S. Application Data

[63] Continuation of Ser. No. 536,996, Sep. 29, 1983, abandoned.

[30] Foreign Application Priority Data

Apr. 27, 1983 [DE] Fed. Rep. of Germany ....... 3315272

[51] Int. Cl.⁴ ............................................. A61K 9/70
[52] U.S. Cl. .................... 424/443; 604/890; 424/447;
[58] Field of Search ............... 604/897, 890, 896; 424/443, 447; 128/155

[56] References Cited

U.S. PATENT DOCUMENTS

| | | | |
|---|---|---|---|
| 3,598,122 | 8/1971 | Zoffaroni | 604/897 |
| 4,286,592 | 9/1981 | Chandrasekaran | 604/897 |
| 4,289,795 | 9/1981 | Bogentoft et al. | 424/471 |
| 4,297,995 | 11/1981 | Golub | 604/897 |
| 4,314,557 | 2/1982 | Chandrasekaran | 604/307 |
| 4,341,759 | 7/1982 | Bogentoft et al. | 424/494 |

FOREIGN PATENT DOCUMENTS 59-84817 5/1984 Japan.

Primary Examiner—John Kight
Assistant Examiner—Garnette D. Draper
Attorney, Agent, or Firm—Dennis P. Clarke

[57] ABSTRACT

The present invention is related to a pharmaceutical product preferably in medical bandage form, for the controlled release of a therapeutically active agent or several such agents to the skin. The pharmaceutical product of the invention consists of an impermeable backing layer, a particularly composed supersaturated reservoir layer for the therapeutically active agent connected therewith and comprising a polymer matrix wherein the therapeutically active agent is soluble and which is permeable to the active agent, an adhesive layer connected with the reservoir layer and permeable to the active agent, and a cover layer covering and adhering to said adhesive layer and removable therefrom for the use of the pharmaceutical product as transdermal therapeutic system, said reservoir layer for the therapeutically active agent consisting of a multitude of layers wherein the concentration of the therapeutically active agent increases from layer to layer with increasing distance from the adhesive layer, and process for producing such a pharmaceutical product.

20 Claims, 2 Drawing Sheets

SECTION THROUGH A LAMINATE WITH A RESERVOIR
LAYER CONSISTING OF TWO INDIVIDUAL LAYERS

SECTION THROUGH A LAMINATE WITH A RESERVOIR LAYER CONSISTING OF TWO INDIVIDUAL LAYERS

SECTION THROUGH A LAMINATE WITH A RESERVOIR LAYER CONSISTING OF FIVE INDIVIDUAL LAYERS

PHARMACEUTICAL PRODUCT, IN MEDICAL BANDAGE FORM

This application is a continuation of 06/536,996 filed Sept. 29, 1983, now abandoned.

The present related to a pharmaceutical product for the administration of therapeutically active agents to and through the skin. This product preferably is in the form of a medical bandage.

The administration of therapeutically active agents to the skin for instance of human beings from medical bandage-like products is known. It is the purpose of this kind of administration to obtain in particular in transdermal administration a release of active agent as uniform as possible over a prolonged period of time and to obtain thereby an uptake of the active agent through this skin as uniform as possible. The control of active agent release from the medical bandage into the skin has at first been achieved by providing a particular membrane on the reservoir for the active agent towards the skin controlling the drug release rate (see for instance German patent No. 2,035,533; U.S. Pat. Nos. 3,598,122 and 3,797,494). The release of active agent occurs by membrane controlled diffusion. The role of the controlling membrane may also be achieved by a pressure-sensitive adhesive coating, as described in European patent publication No. 33615. In this way it is possible to avoid the relatively expensive and complicated controlling membrane. However, in order to obtain medical bandages in a size necessary for the intended long-term treatment and acceptable for the patient, limitations in the possible dosages per medical bandage unit cannot be avoided.

In German patent publication DE-OS No. 3119752 a similar system is described. However, the speed of dissolution of the active agent in the reservoir layer is controlling for the release rate of the active agent from the system. Furthermore, the practical use of this system however shows that with this embodiment of medical bandage there is a limitation of the amount of active agent releasable per bandage unit and there is no uniformity of active agent release.

Furthermore, in German patent publication DE-OS No. 2920500 a transdermal system is described where in a swellable polymer foil with a single reservoir layer the concentration of active agent decreases from the release surface in order to get a uniform release rate. It has been proposed furthermore in this prior art to combine several films of this type. However, the same active agent concentration profile is present in each layer. The particular active agent concentration profile in this unilayer film is produced by diffusion of a solution or suspension of the active agent from one surface of the film into the film and removal of the solvent or, respectively, suspension agent. This process has the considerable disadvantage that the desired active agent concentration profile in the film may reprudced only with considerable technical difficulty.

It is a further disadvantage in this process that the active agent uptake of the film is limited by its adsorption capability. Furthermore, the combination of several such films yields in so complicated conditions that a uniform release of active agent can no more be reached. It is therefor an object of the present invention to avoid these disadvantages and to provide a pharmaceutical product, preferably in medical bandage form, which may be produced in a simple and cheap manner and which allows a reproducible controlled active agent release over the complete time of use and which also allows a change in the release rate.

The pharmaceutical product according to the present invention, preferably in medical bandage form, for controlled release of one or several therapeutically active agents to the skin consists, as is known, of (a) an impermeable backing layer, (b) a reservoir layer adjacent to and in close contact with, this backing layer and supersaturated with the therapeutically active agent or agents said reservoir layer comprising a polymer matrix wherein the therapeutically active agent or agents are soluble and which is permeable to said agent or agents, (c) an adhesive layer adjacent to and in close contact with, said reservoir layer and permeable to said therapeutically active agent or agents and (d) a cover layer covering and adhering to said adhesive layer and removable therefrom for the use of said pharmaceutical product as transdermal therapeutic system.

The pharmaceutical product according to the present invention is characterized in that the reservoir layer for the therapeutically active agent or agents consists of a multitude of individual layers and that the concentration of the therapeutically active agent or agents in these individual layers increases from individual layer to individual layer with increasing distance from the adhesive layer. In another embodiment of the present invention there is provided an additional adhesive layer between the impermeable backing layer and the supersaturated reservoir layer.

In the attached drawings

Figure 1:
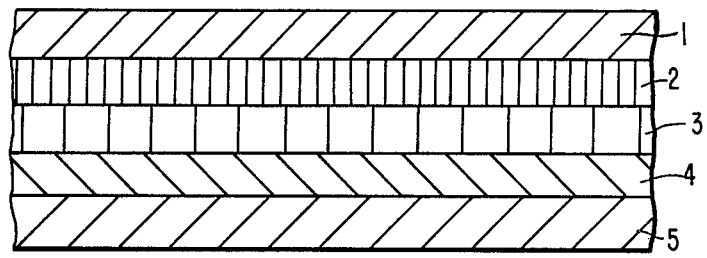
FIG. 1 shows a cross section of a pharmaceutical product according to the present invention with a two-layer reservoir (the shown layer thicknesses are not corresponding to the actual thickness)

FIG. 1 shows a cross section through the embodiment having a two-layer-reservoir. The backing (1) is the most outer layer of the laminate. This layer is a protective layer and the structural base of the pharmaceutical product and substanstially avoids the loss of any component of the individual layers (2) and (3).

The backing layer (1) is followed by the first reservoir layer (2). This layer is immediately below the backing layer and is in close contact with the inner surface of the backing layer. This first reservoir layer is immediately followed by a second reservoir layer. Both reservoir layers (2) and (3) consist of a polymer matrix which in each layer may be equal or different from each other and which both are supersaturated with the active agent contained therein. The content of active agent in both layers is such that it is larger in layer (2) then in layer (3). This is graphically shown in figure (1) by a different hatching.

Immediately after the reservoir layer (3) follows an adhesive layer (4) permeable for the active agent or agents. This layer is to affix the product tensily on the skin. If necessary, it may be loaden also with active agent during the production, the concentration however being smaller or only equal the saturation concentration The adhesion layer (4) is followed by a cover layer which immediately before use is peeled off and removed.

This layer of produced from a material which is not permeable for any of the components of the pharmaceutical product.

Figure 2:
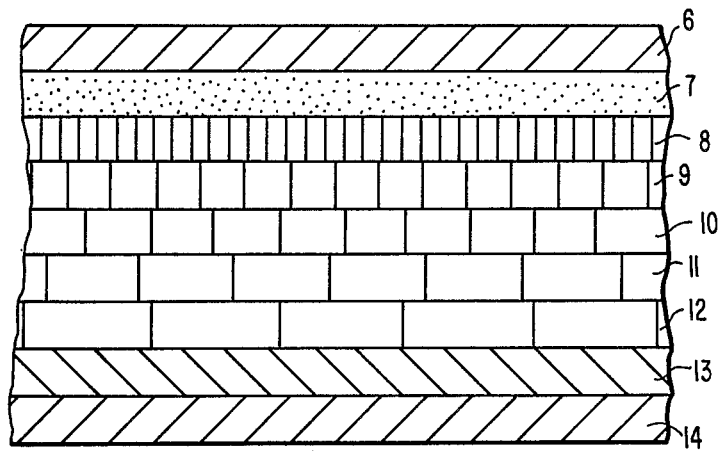
FIG. 2 shows a cross section of a different embodiment with a five-layer reservoir (the shown layer thicknesses do not correspond to the actual thickness)

FIG. 2 shows a cross section of another embodiment according to the present invention with a reservoir built up of five individual layers. Different from FIG. 1, there is provided an additional adhesive layer (7) between the backing layer (6) and the most upper reservoir layer (8). Such an additional adhesive layer is preferred and therefor provided in accordance with the present invention if there is no sufficient adhesive power between the most upper layer of the drug reservoir and the backing layer. The reservoir in this embodiment consists of the five layers (8) to (12) which all are supersaturated with the therapeutically active agent. The content of each layer decreases from layer (8) to layer (12) (see difference in hatching). Layer (12) is followed by an adhesive layer (13) permeable to the active agent or agents which layer then is followed by the removable protective layer.

Figure 3:
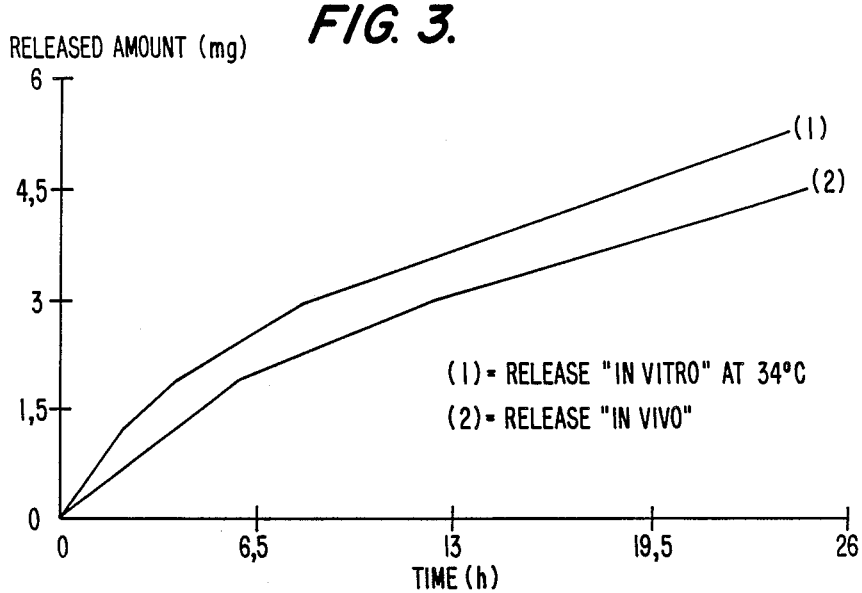
FIG. 3 shows a graphical diagram of the release of nitroglycerin from a medical bandage according to the present invention over the time.
Figure 4:
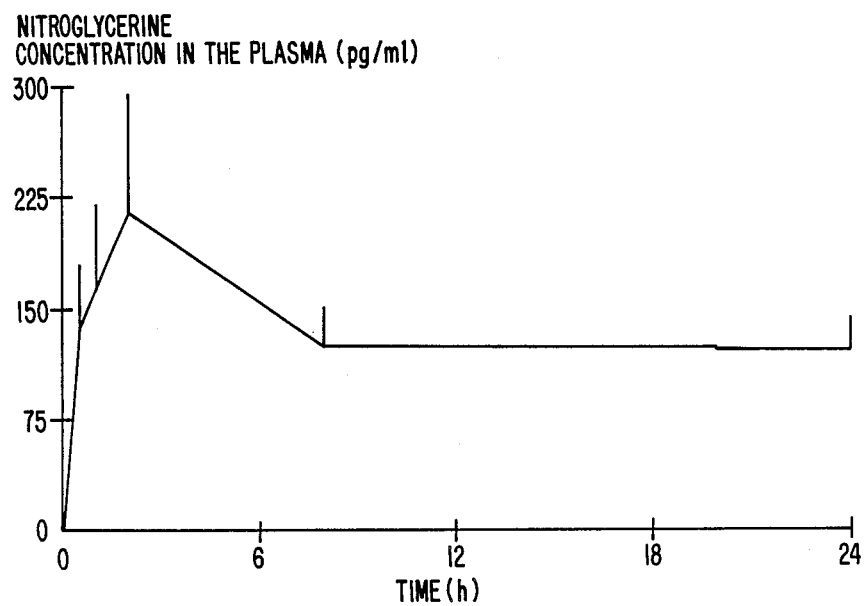
FIG. 4 shows the plasma concentration of nitroglycerin as obtained with a medical bandage according to the present invention over the time.

FIGS. 3 and 4 are further explained in Example 1.

The backing layers (1) or, respectively, (6) may be produced from a flexible or non-flexible material and may have a unilayer or multilayer structure. Materials which may be used for their production are polymers such as polyethylene, polypropylene, polyethyleneterephthalate, polyamide. Furthermore, metal foils such as aluminum foils may be used alone or coated with any of the above polymer materials. Further more, the backing layer may also be of textile material if the components of the reservoir layer physically allow such backing material and do not penetrate through textile materials. In a preferred embodiment, the backing layer (1) or, respectively, (6) is of a compact material giving the pharmaceutical product the structural stability and serving as a barrier against the loss of components of the pharmaceutical product according the the present invention. Furthermore, there may be used foils or compact materials coated by aluminum by damping.

The reservoir layers (2) and (3) or, respectively, (8) to (12) consist of a polymer matrix and the therapeutical agent or agents the polymer matrix having such an adhesiveness assuring to keep together the individual reservoir layers. The polymer matrix consists of a base polymer and usual additives. The choice of base polymer depends upon the chemical and physical properties of the used therapeutically active agent or agents. For instance, useful polymers are caoutchouc and caoutchouc-like synthetic homo-, co- or graft polymeres, polyacrylic acid esters and their copolymers, polyurethane and silicon rubbers. All polymers may be used which have been used in the production of pressure sensitive adhesive materials and which are physiologically acceptable.

The kind of additives depends upon the used polymer and upon the therapeutically active agent or agents. There may be plasticizers, agents improving the adhesive power, resorption improving agents, carrier materials, stabilizing agents and fillers. Products which may be used for this purpose and which are physiologically acceptable are known to the expert in the art.

Furthermore, there may be present in the polymer matrix carrier agents for the therapeutically active agent which add to the stabilization of the system and the use of the therapeutically active agent or agents such as lactose in the use of nitroglycerin-lactose-mixtures.

The transdermal therapeutic system according to the present invention may be applied to many therapeutically active agents which are administered to the skin with or without resorption improving agents and which produce a local or systemic activity. Active agents which produce a local effect are, for instance, however without limiting the invention hereto, agents against transpiration, fungicides, bactericides and bacteriostatics.

Therapeutically active agents which produce a systemic activity are, for instance, without however limiting the invention hereto, antibiotics, hormons, antipyretics, antidiabetics, coronar dilatatory agents, heart active glycosides, spasmolytics, antihypertonic, psychopharmaca, antimigraine agents, corticosteroides, analgetics, anticontraceptives, antirheumatics, anticholinergic agents, sympatolytics, sympatomimetics, vasodilatatory agents, anticoagulantives, antiarrhytmetics.

The increase of active agent concentration in the individual layers of the reservoir may cause a decrease in the adhesive power between the outer surface of the reservoir layer and the backing layer which is necessary for the structural stability of the system. In this case, according to the present invention, the structural stability is improved by providing an additional adhesive intermediary layer (7). This layer may be produced from the same material as the polymer matrix without however the resorption improving agents and carrier materials.

The adhesive layer (4) or, respectively, (13) producing the contact to the skin consists of an adhesive material which is physiologically acceptable and which is permeable to the therapeutically active agent or agents in the reservoir layer. Polymer materials useful for this layer may be selected from the list of polymer materials given for the reservoir layer. In order to allow the desired drug release right from the beginning of the use of the pharmaceutical product according to the invention it may be necessary to incorporate into this adhesive layer the active agent or agents during the production of the pharmaceutical product. In this case the active agent concentration is to be lower than, or equal to, the saturation concentration.

The removable or peelable cover layer (5) or, respectively, (14) adjacent to and adhearing to the adhesive layer and which is to be peeled off before use, consists for instance of the same materials as they are used for the backing layer (1) or, respectively, (6), provided however that they are rendered removable from the adhesive layer, for instance by adding a usual silicon coating before application to the adhesive layer. Further materials useful for the production of removable cover layer are for instance polytetrofluoroethylene, paper treated and coated with such material, cellophan, polyvinylchloride or the like. If the pharmaceutical product according to the present invention is cut to for instance medical bandages before application of the cover layer, the then to be applied cover layer cuts may have a projecting part easing the removal of the cover layer from the medical bandage.

Surprisingly, a medical bandage according to the present invention combines all desirable biopharmaceutical and technological properties of a therapeutic system as discussed hereinafter:

1. Control release of active agent

The total of all features of the medical plaster according to the present invention assures a substantially uniform release in active agent for most of the time of administration. If a peak release in the first part of the period of administration is desired, active agent is incorporated into the adhesive layer too.

2. Controllability of the release rate of active agent

The desired rate of release of active agent during the intended time of administration may be controlled in a wide range by the following:

Composition of the polymer matrixes, total of concentration of active agent in the reservoir and, possibly, adhesive layer, active agent concentration gradiant over the individual layers of the reservoir layer, number of the individual layers of the reservoir layer, thickness of the individual layers of the reservoir layer, size of the medical plaster, kind and amount of carrier agents added to the reservoir layer.

Some or all of these feature may be individually adjusted thereby allowing to meet all desired medical needs.

3. Controllability of the release time

The duration of the therapeutically necessary release rate may be controlled by the chosen proportion between the amount of active agent in the pharmaceutical product and the average release rate.

4. Dosing

Contrary to prior art medical plasters, the dosage per unit of surface area of the adhesive layer is practically not limited in the present medical plaster, obviously due to the particular structure of the reservoir layer as a set of a multitude of individual layers each individual layer being supersaturated with the therapeutically active agent or agents and the particular increase of the concentration of active agent or, respectively, agents from individual layer to individual layer and with increasing distance from the adhesive layer. Furthermore, local irritations on the skin quite often occuring by too high a concentration in active agent, are avoided by the fact that the first individual layer closest to the skin of the treated person is separated from the skin by an adhesive layer which to the most is saturated in active agent or agents, thus avoiding a direct contact of undissolved active agent or agents with the skin.

5. Possibilities to vary the drug releasing surface

Since the pharmaceutical product according to the present invention neither needs lateral walls nor covers nor edge tightening, it may be produced deliberately as large as necessary and in form according to the therapeutical requirements. This is of particular importance where the treatment is started with a minimum dosage, said dosage being slowly increased to the regular dosage or where a treatment is finished with a slowly decreasing dosage.

6. In vitro- in vivo-correlation of drug release

Surprisingly, the pharmaceutical product according to the present invention fulfills the high prerequisites with respect to the in vitro and in vivo drug release. The correlation of in vitro drug release to in vivo drug release is so satisfactory that in vitro test models are most analogous. This allows a secure checking of the reproducability of charges and of bioequivalence.

The structure of the pharmaceutical product according to the present invention is further illustrated hereinafter:

The number of individual layers in the drug reservoir layer is chosen according to the demands. The lowest limit as per definition is 2 individual layers, the upper limit is determined by practical and economical reasons at 12. In a preferred embodiment of the present invention the number of the individual layers is between 2 to 6. The individual layers are of equal or differing thickness, each individual layer having a thickness between from 0.005 to 5.0 mm. Preferably, the thickness of the individual layers is between 0.01 to 0.5 mm.

The adhesive layer has a layer thickness of from 0.005 to 3.0 mm, preferably 0.01 to 0.5 mm.

The various individual layers of the reservoir layer may be produced from one and the same polymer matrix or the individual layers may be produced from differing polymer matrixes. The amount of therapeutically active agent or agents in the total reservoir layer corresponds to up to the tenfold of the therapeutically desired amount. This therapeutically desired amount is determined by the kind of the active agent or agents, the intended time of the application of the medical bandage and the intended therapeutical field or therapeutical indication for the pharmaceutical product.

The ratio of drug concentration in g per $cm^3$ in the individual layer of the supersaturated reservoir layer adjacent to the adhesive layer to the drug concentration in the individual layer of the supersaturated reservoir layer closest to the cover layer is within the range of 1:1.1 to 1:20, preferably 1:2 to 1:20.

The pharmaceutical product according to the present invention is produced applying known technologies in this field. Thus, at first the adhesive layer permeable to the therapeutically active agent or agents is coated to the removable cover layer. Onto this layer are coated the various individual layers of the supersaturated reservoir layer and finally there is coated the final impermeable backing layer onto the last individual layer of the supersaturated reservoir layer. According to the invention there is coated onto the adhesive layer one individual layer of the supersaturated drug reservoir layer and, at least, thereto one further individual layer of the supersaturated reservoir layer wherein the therapeutically active agent or agents are present at a higher concentration in g per $cm^3$ than in the previously coated individual reservoir layer. If desired or necessary, an additional adhesive layer is coated on the last individual reservoir layer before application of the impermeable backing layer. In another embodiment of the present process, the layers may be coated onto each other in reciprocal sequence, i.e. starting with the backing layer, continuing with the individual layer of the reservoir layer having the highest concentration in active agent and continuing with the other individual layers of the reservoir layer with decreasing drug concentrations in each individual layer, then the adhesive layer and finally the removable cover layer.

The adhesive layer, intermediary layer and/or various individual layers of the reservoir layer are produced by laminar distribution of the components of the layers containing additionally a solvent or dispersing agent and removing the solvent or, respectively, dispersing agent to the greatest extent before coating the next layer on to it. Another possibility for producing the various layers consists in converting the components of the layer without solvent or dispersing agent into flat parts from a melt thereof by known methods and to line the various layers on to each other thus forming a laminate. The heat stability of all components at the necessary procedure temperature is a prerequesite for this embodiment of the production of the pharmaceutical product of the present invention.

The following Examples serve to further illustrate the present invention without however limiting the same thereto.

EXAMPLE 1

A pharmaceutical product according to the present invention having a reservoir layer consisting of three individual layers is produced as follows:

The material for the adhesive layer containing nitroglycerine is produced from 0.175 kg of polyisobutylene (mean molecular weight between 900,000 to 1,400,000. Trade product OPPANOL B 100)

0.157 kg of solid aliphatic hydrocarbon resin (trade product PICCOTAC CBHT)

0.157 kg of hydrogenated rosin resin (trade product ABITOL)

0.0105 kg of 5 percent solution of nitroglycerine in a triglycerid of medium-size chain in the ether hydrocarbon group (trade product MIGLYOL 812), 1.174 kg of special gasoline 80–100 as solvent This product is coated onto the one side of a cover layer having an aluminum layer unilaterally vapour deposited thereon and an adhesive layer at both surfaces such that after evaporation of the solvent a layer of about 20 g per square meter is obtained. Onto this adhesive layer there is coated the first reservoir layer again at a weight per unit of area of about 20 g per square meter.

This reservoir layer is produced by coating a dispersion consisting of 0.05 kg of a 10 percent (weight/weight) nitroglycerinelactose-distribution, 0.153 kg of polyisobutylene (mean molecular weight of 900,000 to 1,400,000; trade product OPPANOL B 100), 0.137 kg of solid aliphatic hydrocarbon resin (trade product PICCOTAC CBHT), 0.137 kg of hydrogenated rosin resin (trade product ABITOL)

0.01 kg of triglycerid as solvent (trade product MIGLYOL 812), 1.148 kg of special gasoline 80–110 as solvent.

This product is coated to a separating paper and the dispersion agent and solvent is evaporated thereafter.

In the same way there is produced the bulk material for the second reservoir layer from the following products and coated onto the above first reservoir layer:

0.6 kg of a 10 percent (weight/weight) nitroglycerinelactose-distribution, 0.2 kg of solid aliphatic hydrocarbon resin (trade product PICCOTAC CBHT), 0.2 1 kg of hydrogenated rosin resin (trade product ABITOL), 0.025 kg of triglyceride as solvent (trade product MIGLYOL 812), 1876 kg of the special gasoline 80–110 as solvent.

Correspondingly, there is produced the bulk material for the third individual reservoir layer from:

2.5 kg of a 10 percent (weight/weight) nitroglyerinelactose-distribution, 0.857 kg of polyisobutylene (mean molecular weight of 900,000 to 1,400,000; trade product OPPANOL B 100), 0.77 kg of solid aliphatic hydrocarbon resin (trade product PICCOTAC CBHT), 0.77 kg of hydrogenated rosin resin (trade product ABITOL), 7.507 kg of the special gasoline 80-110 as solvent, 0.1 kg of triglycerid as solvent (trade product MIGLYOL 812).

For obtaining a total weight per area unit of about 200 g per square meter, the dispersion is coated onto the separating paper in three consecutive steps. The thus produced third individual layer material is coated onto the second individual reservoir layer.

In a corresponding manner, the additional adhesive intermediary layer is produced with a weight per unit of area of about 20 g per square meter from a mixture of the following components.

0.179 kg of polyisobutylene (mean molecular weight 900,000 to 1,400,000; trade product OPPANOL B 100), 0.16 kg of solid aliphatic hydrocarbon resin (trade product PICCOTAC CBHT), 0.16 kg of hydrogenated rosin resin (trade product ABITOL), 1.167 kg of the special gasoline 80-110 as solvent.

This material is coated onto the third individual reservoir layer.

After finally covering the additional adhesive intermediary layer with an impermeable backing layer, the resulting laminate is divided into the singular medical plasters in accordance with the therapeutic reguests.

Stability tests

The stability is determined with cuts of the above laminate measuring 4 by 4 centimeter (=16 square centimeter). They have been stored in the open atmosphere for 12 weeks at 31° C. or 40° C. and 70 percent relative humidity. The results of these stability tests are summarized in the following table:

TABLE I

| Period of storage (weeks) | Nitroglycerine content (%) (mean values ± rel. S.D., n = 3) | |
|---|---|---|
| | 31° C. | 40° C. |
| 0 | 100 ± 1.83 | 100 ± 1.83 |
| 2 | 100.8 ± 0.57 | 100.3 ± 2.1 |
| 4 | 98.3 ± 0.55 | 95.3 ± 0.5 |
| 8 | 99.2 ± 3.17 | 94.9 ± 0.5 |
| 12 | 99.7 ± 0.77 | 97.2 ± 0.58 |

Release of therapeutically active aqent 1. in vitro test

A piece of the laminate measuring 16 square centimeters ($cm^2$) and produced in accordance with Example 1, after removal of the cover layer, is dipped into an isotonic sodium chloride solution at 34° C. and the amount of released nitroglycerine is determined at predeterminded time intervals by liquid chromatography. The volume of the extraction medium is chosen such that sink conditions are maintained over the total time of the test.

2.1 in vivo test

For each administration three medical plasters, each 16 square centimeter large, produced in accordance with Example 1, are stuck to the chest skin of the test person. After 6, 12 and 26 hours, respectively, one of the medical plasters is pulled off and the nitroglycerine content remaining in the medical plaster is determined chromatographically.

2. in vivo test

A 16 square centimeter medical plaster produced according to Example 1 is stuck to the chest skin each of 6 test persons. After 24 hours the medical plaster is pulled off and the nitroglycerine content which remained in the medical plaster is determined chromatographically. The mean value of released nitroglycerine was $5.0 \pm 0.7$ mg per 24 hours. Thus, the in vitro test and in vivo test described hereinabove in para. 1 and 2.2 show that there is an excellent in vitro/in vivo-correlation between the amounts of released active agent.

The results are graphically demonstrated in FIG. 3. The curves (1) and (2) demonstrating the amount of released active agent show that during the therapeutically intended duration of 24 hours, the nitroglycerine is released from the medical plaster according to the present invention in a controlled and continuous manner, the release rate being almost constant over almost 20 hours.

Bioavailability

Blood samples were taken from the test persons involved in the above tests 0.5, 1, 2, 8 and 24 hours after administration and nitroglycerine concentration in the blood plasma was determined by capillary gas chromatography. The results are shown in FIG. 4. According thereto, the nitroglycerine concentrations are within the therapeutically active dosage range during the duration of administration.

EXAMPLE 2

Example 1 was repeated: using a semi-liquid aliphatic hydrocarbon resin in place of the hydrogenated rosin resin, the amounts of the various components being identical otherwise. The coating and sequence of coating is identical with that described in Example 1.

The results of the in vitro test and in vivo test for active agent release are the same as in Example 1. The rate of in vitro release in 24 hours amounted to 3.5 mg.

EXAMPLE 3

Another pharmaceutical product according to the present invention is produced having a reservoir layer composed of two individual layers:

The nitroglycerine containing adhesive layer bulk material consisted of:
20 g of polyisobutylene (mean molecular weight 900,000 to 1,400,000; trade product OPPANOL B 100),
18 g of the solid hydrogenated hydrocarbon resin (trade product PICCOTAC CBHT),
12 g of the liquid hydrogenated hydrocarbon resin (trade product ADTAC),
1 g of a 5 percent solution of nitroglycerine in a triglyceride (trade product MIGLYOL 812),
119 g of n-hexane as solvent.

This bulk material is coated to a cover layer which was unilaterally damped with aluminum and on both sides provided with an abhesive lining. The bulk material for the adhesive layer is coated onto the cover layer in such an amount that after evaporation of the solvent a layer weight per unit of area is obtained amounting to about 20 g per square meter.

The first individual layer of the reservoir layer is coated onto the thus obtained adhesive layer at a weight per unit of area of about 200 g per square meter. The bulk material for this individual layer of the reservoir layer consisted of:
33,8 g of polyisobutylene (mean molecular weight 900,000 to 1,400,000; trade product OPPANOL B 100),
30.44 g of the solid hydrogenated hydrocarbon resin (trade product PICCOTAC CBHT),
20.30 g of the liquid hydrogenated hydrocarbon resin (trade product ADTAC),
28,75 g of a 10 percent (weight/weight) nitroglycerine lactose distribution,
1.69 g of a triglyceride (trade product MIGLYOL 812),
179.0 g of n-hexane as dispersion agent.

Until reaching a total weight per unit of area of about 20 g per square meter, the above dispersion is coated onto the separation paper in two consecutive steps.

In a corresponding manner, the second reservoir layer having a weight per unit of area of about 100 g per square meter is produced from the following bulk material:
34.3 g of polyisobutylene (mean molecular weight 900,000 to 1,400,000; trade product OPPANOL B 100),
30.9 g of the solid hydrogenated hydrocarbon resin (trade product PICCOTAC CBHT),
20.6 g of the liquid hydrogenated hydrocarbon resin (trade product ADTAC),
87.5 g of a 10 percent (weight/weight) nitroglycerinelactose-distribution,
1.7 g of a glycerine (trade product MYGLYOL 812),
247.0 g of n-hexane as dispersing agent.

This individual layer of the reservoir layer is coated onto the first individual layer of the reservoir layer.

In a corresponding manner, the additional adhesive intermediary layer having a weight per unit of area of about 4 g per square meter is produced from the following cco components:
20.0 g of polyisobutylene (mean molecular weight 900,000 to 1,400,000; trade product OPPANOL B 100),
18.0 g of the solid hydrogenated hydrocarbon resin (trade product PICCOTAC CBHT),
12.0 g of the liquid hydrogenated hydrocarbon resin (trade product ADTAC),
119.0 g of n-hexane.

This bulk material is coated onto the second individual layer of the reservoir layer.

After covering the additional adhesive intermediary layer with an impermeable backing layer, the resulting laminate is divided into singular pieces in accordance with the therapeutical demands.

Again, the in vitro release rates and in vivo release rates of nitroglycerine are determined as described in connection with Example 1. The release rate in vitro and in vivo were 3.5 mg or, respectively, 3.0 mg within 24 hours. With this product again a continuous and controlled release of nitroglycerine is determined.

We claim:

1. In a pharmaceutical product, in medical bandage form, for the controlled release of one or several therapeutically active agents to the skin comprising:
   (a) an impermeable backing layer,
   (b) a reservoir layer adjacent to and in close contact with said backing layer, said reservoir layer comprising a polymer matrix wherein said therapeutically active agent or agents are soluble and which is permeable to said agent or agents,
   (c) an adhesive layer adjacent to, and in close contact with, said reservoir layer and permeable to said therapeutically active agent or agents, and
   (d) a cover layer covering and adhering to said adhesive layer and removable therefrom for the use of said pharmaceutical product as a transdermal therapeutic system,
the improvement wherein said reservoir layer for the therapeutically active agent or agents consists of a multitude of individual layers, each layer having a concentration of said therapeutically active agent or agents above saturation and the concentration of the therapeutically active agent or agents in said individual layers increasing from individual layer to individual layer with increasing distance from said adhesive layer.

2. The pharmaceutical product as claimed in claim 1, additionally having an adhesive layer between said impermeable backing layer and said reservoir layer.

3. The pharmaceutical product as claimed in claim 1, wherein said reservoir layer consists of 2 to 12 individual layers.

4. The pharmaceutical product as claimed in claim 1 wherein said reservoir layer consists of 2 to 6 individual layers.

5. The pharmaceutical product as claimed in claim 1 wherein said individual layers are equal or different in their individual thickness, the thickness of each individual layer being in the range of from 0.005 to 5.0 mm.

6. The pharmaceutical product as claimed in claim 2 wherein said individual layers of the reservoir layer are equal or different in their individual thickness, the thickness of each individual layer being in the range of from 0.005 to 5.0 mm.

7. The pharmaceutical product as claimed in claim 4 wherein said individual layers are equal or different in their individual thickness, the thickness of each individual layer being in the range of from 0.01 to 0.5 mm.

8. The pharmaceutical product as claimed in claim 5 wherein said adhesive layer has a thickness in the range of from 0.005 to 3.0 mm.

9. The pharmaceutical product as claimed in claim 6 wherein said adhesive layer has a thickness in the range of from 0.005 to 3.0 mm.

10. The pharmaceutical product as claimed in claim 7 wherein said adhesive layer has a thickness in the range of from 0.01 to 0.5 mm.

11. The pharmaceutical product as claimed in claim 1 wherein the polymer matrix comprises one or several usual additives selected from the group consisting of the plasticizers, the adhesive agents, the resorption improving agents, the carrier materials, the stabilizing agents, and the fillers.

12. The pharmaceutical product as claimed in claim 1 wherein the individual layers forming the reservoir layer are equal or different in polymer matrix material.

13. The pharmaceutical product as claimed in claim 1 wherein the amount of therapeutically active agent or agents in the reservoir layer is up to the tenfold of the therapeutically necessary amount which is determined by the type of therapeutically active agent or agents, the intended duration of administration and the intended field of pharmaceutical use for the therapeutically active agent.

14. The pharmaceutical product as claimed in claim 1 or claim 2 wherein the proportion between the concentration of the therapeutically active agent or agents in g per $cm^3$ in the individual layer of said reservoir layer adjacent to said adhesive layer and the concentration of the therapeutically active agent or agents in the individual layer adjacent to said backing layer or, respectively, said additional adhesive layer, is in the range of from 1:1.1 to 1:20.

15. The pharmaceutical products as claimed in claim 14 wherein said proportion is in the range of from 1:2% to 1:20.

16. Process for the production of a pharmaceutical product as claimed in claim 1 or claim 2 wherein there is coated onto a removable cover layer said adhesive layer permeable to the therapeutically active agent or agents to be incorporated into the pharmaceutical product, there then are coated consecutively onto said adhesive layer the various individual layers of said reservoir layer, first the individual layer with the lowest concentration in therapeutically active agent or agents and thereafter the individual layers with increasing concentration in therapeutically active agent or agents, if desired, there thereafter is coated the additional adhesive layer and finally said lacking layer, or wherein the coating procedure is effected in the contrary sequence starting with said backing layer and finalizing with said removable cover layer.

17. Process as claimed in claim 16 wherein there are used individual coating layer materials for building up said reservoir layer the concentration of the therapeutically active agent or agents in said individual layer materials being such that the proportion between the concentration of the therapeutically agent or agents in g per $cm^3$ in the individual layer of said reservoir layer adjacent to said adhesive layer and the concentration of the therapeutically active agent or agents in the individual layer adjacent to said backing layer or, respectively, said additional adhesive layer is in the range of from 1:1.1 to 1:2.

18. Process as claimed in claim 16 or claim 17 wherein the material for the adhesive and/or the reservoir layers comprises solvent or, respectively, dispersion agent when being used in the coating step, said solvent or dispersion agent is substantially completely removed from said coating material in each coating step before the next coating step is effected.

19. Process as claimed in claim 16 wherein one or several of the various coatings is applied by lining.

20. Process as claimed in claim 16 wherein all of the individual layers are produced from a melt of the layer material in each instance.

* * * * *

UNITED STATES PATENT AND TRADEMARK OFFICE
CERTIFICATE OF CORRECTION

PATENT NO. : 4,769,028

DATED : September 6, 1988

INVENTOR(S) : Hans R. Hotfmann; Reinhold Meconi, Michael Wolff; Horst Zerbe

It is certified that error appears in the above-identified patent and that said Letters Patent is hereby corrected as shown below:

Claim 15, column 12, line 22, after 1.2, delete "%".

Claim 16, column 12, line 36, change "lacking" to --backing--.

Claim 17, column 12, line 51, change "1.2" to read --1:20--.

Signed and Sealed this

Fourteenth Day of March, 1989

*Attest:*

DONALD J. QUIGG

*Attesting Officer*  *Commissioner of Patents and Trademarks*